United States Patent [19]

Kalopissis et al.

[11] 4,061,730
[45] Dec. 6, 1977

[54] ANTI-SOLAR AGENT AND COMPOSITIONS CONTAINING THE SAME

[75] Inventors: Gregoire Kalopissis, Paris; Claude Bouillon, Eaubonne; Charles Vayssie, Aulnay-sous-Bois, all of France

[73] Assignee: Societe Anonyme dite: L'Oreal, Paris, France

[21] Appl. No.: 656,573

[22] Filed: Feb. 9, 1976

Related U.S. Application Data

[63] Continuation of Ser. No. 397,978, Sept. 17, 1973, abandoned.

[30] Foreign Application Priority Data

Sept. 25, 1972 Luxembourg .............. 66156

[51] Int. Cl.² ............... A61K 7/42; C07C 87/68
[52] U.S. Cl. .................. 424/59; 260/567.6 M
[58] Field of Search ............ 424/59; 260/567.6 M

[56] References Cited

U.S. PATENT DOCUMENTS

| 3,647,880 | 3/1972 | Blumenthal | 424/59 |
| 3,981,417 | 12/1973 | Welters et al. | 424/59 |

FOREIGN PATENT DOCUMENTS

| 2,000,142 | 11/1969 | France | 424/59 |
| 676,103 | 5/1939 | Germany | 424/59 |
| 39,639 | 12/1970 | Japan | 424/59 |

OTHER PUBLICATIONS

Chem. Abs., 1963, pp. 9150 to 9152.

Primary Examiner—Dale R. Ore
Attorney, Agent, or Firm—Cushman, Darby & Cushman

[57] ABSTRACT

An anti-solar cosmetic composition contains as the anti-solar agent a compound of the formula

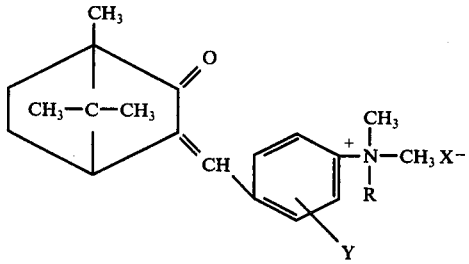

wherein R is hydrogen or alkyl containing 1-12 carbon atoms, Y is hydrogen, methyl or halogen and X is halide, arylsulfonate, alkylsulfonate, camphosulfonate or alkyl sulfate. The antisolar agent is present in amounts of 0.05–10 percent by weight of said composition.

13 Claims, No Drawings

ANTI-SOLAR AGENT AND COMPOSITIONS CONTAINING THE SAME

This is a continuation, of application Ser. No. 397,978 filed Sept. 17, 1973, now abandoned.

The invention relates to new compounds capable of absorbing ultra-violet rays of a specific range which make such compounds ideally suited for use not only in antisolar cosmetic compositions for the protection of human skin from harmful effects of actinic rays but also as a preservative for cosmetic preparations susceptible to degradation or discoloration by exposure to light waves.

It is known, for instance, that sunburn, or erythema, results from the excessive exposure of human skin to the rays of the sun and the wave lengths of light in the range of 280–315 millimicrons, often called the "erythematous zone," are those which produce such sunburn. Below this wave length range the sun rays do not present any particular danger, for they are filtered by the ozone in the atmosphere. However, the UV rays which are responsible for or which produce a desirable suntan are those in the zone ranging from 315 to 400 millimicrons.

Consequently, if one desires to be exposed to solar radiation, it is important that the skin be protected with the aid of a composition containing a substance which absorbs the UV rays in the erythematous zone, thereby avoiding an undesirable sunburn, which composition however also transmits those wave lengths in the range of 315 to 400 millimicrons so as to obtain a desirable suntan. In particular, it is necessary to transmit those rays of wave lengths in the neighborhood of 340 millimicrons, which imparts maximum browning of the skin without erythema.

Thus, the protective agent must exhibit a high absorbency power between 280–315 millimicrons, and a weak absorbency power above 315 millimicrons. In addition to this critical absorbing power, the protective agent must have other properties and in particular it should exhibit good resistance to the exterior elements, that is, exhibit good photochemical stability, good thermal stability, and have sufficient affinity for the skin and sufficient chemical stability so as not to be removed or degraded by perspiration or at least by washing.

Further, it is also known that certain dyes often contained in various cosmetic preparations, notably those compositions for the hair such as colored hair dyes and lacquers, shampoos and colored hair setting lotions as well as certain other cosmetic formulations such as nail enamel compositions and colored creams do not always possess sufficient stability to light. These cosmetic compositions are oten provided in the form of a solution, emulsion, gel, suspension, or dispersion, packaged in clear glass or transparent plastic containers and thus can be exposed to light rays not only during use but also during storage. Hair lacquers in particular are frequently packaged in transparent vaporizer containers so as to permit the consumer to view and select the desired color.

Since many of the dye components of these cosmetic compositions do not possess sufficient stability to the light rays, which is particularly the case in the use of triphenylmethane derivatives, such as crystal violet, methyl violet and methyl green, it is known that such cosmetic compositions often are subject to rapid deterioration. This disadvantage has also been experienced with a significant number of other dyes, which though stable under certain concentration conditions, nevertheless exhibit marked photosensitivity when they are used in relatively weak concentrations.

It has also been observed that some essentially colorless cosmetic compositions, for example, colorless nail enamels frequently experience some alteration and turn yellow after prolonged exposure to light.

Thus is has been found that such cosmetic compositions, colored or colorless, can be preserved in storage only for a certain limited period of time, generally in the order only of a few weeks. To overcome these disadvantages, it has been proposed to incorporate in these compositions a compound capable of filtering light rays. Such a compound, however, must not only exhibit good filtering characteristics, but also good stability and a sufficient degree of solubility in the vehicles conventionally employed in these cosmetic compositions. The present invention now provides new compounds having these different criteria which effectively overcome the disadvantages noted above.

Thus it is an object of the present invention to provide a cosmetic composition comprising a cosmetic vehicle and at least one anti-solar agent of the formula

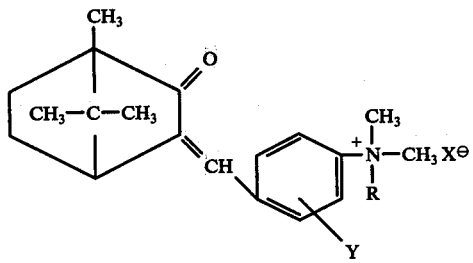

wherein
- R represents a member selected from the group consisting of hydrogen and alkyl having 1–12 carbon atoms,
- Y represents a member selected from the group consisting of halogen, methyl or hydrogen and
- X represents a member selected from the group consisting of halide, arylsulfonate, alkyl sulfonate, camphosulfonate and alkylsulfate.

The present invention also relates to a cosmetic composition for topical application to the skin to protect the skin against those ultra-violet rays which cause erythema or sunburning while at the same time permits browning of the skin. This composition can be provided as a solution in the form of a lotion, as an emulsion in the form of a cream, gel, foam or milk or under any other form conventional for a cosmetic preparation of this type, such as an aerosol. The composition can thus include conventional cosmetic adjuvants such as thickening agents, emollients, superfatting agents, softening agents, wetting agents, surface-active agents, preservatives, anti-foaming agents, perfume and any other component conventionally employed in cosmetic compositions. When the compositions of the present invention are provided in the form of an aerosol, they are packaged under pressure in a conventional aerosol bomb or container in the presence of a propellant gas which is preferably a halogenated hydrocarbon or a mixture of said hydrocarbons, such as, for example, trichlorofluoromethane and dichlorodifluoromethane.

In the compositions of this invention the above defined anti-solar agent is generally present in amounts of 0.5–10% by weight of the composition. As the solvent or cosmetic vehicle there can be used water, a lower alkanol, a lower polyol or an aqueous solution of a lower alkanol. The lower alkanol or lower polyol can be, for instance, ethanol, isopropanol, propylene glycol, glycerol or sorbitol. While the compositions of the present invention are often colorless, it will be appreciated that they can also be colored.

Thus the present invention has also for an object the provision of a cosmetic composition including one or more components which are sensitive to ultra violet rays and notably one or more photosensitive dyes which are generally present in a very weak concentration in the order of 0.001-0.01% of the total weight of the composition. Such compositions contain as a protective agent against the ultra violet rays one or more compounds of formula (I) in amounts of about 0.05-5 percent of the total weight of the composition.

In addition to the dye and the component of formula (I) such compositions can also include one or more of the following cosmetic adjuvants: a surface active agent, a swelling agent, a thickening agent, a softening agent, a superfatting agent, a bleaching agent, a film forming agent, a cosmetic resin, a wetting agent, a foaming agent, a preservative, perfume or any other component conventionally employed in cosmetic compositions.

Representative cosmetic compositions which contain a compound of formula (I) as a filtering agent for ultra violet rays include capillary compositions, particularly hair lacquers, plasticizing hair setting lotions, treating or untangling hair lotions, shampoos, dye shampoos, hair dye solutions, nail enamels, skin creams and dye foundations.

These compositions are also often packaged in clear glass or transparent plastic containers and can also be provided in the form of an aerosol, as noted above.

Further, the present invention also relates to a process for protecting cosmetic compositions susceptible of being altered or deteriorated by light rays comprising incorporating in these compositions a compound of formula (I) in amounts of about 0.05-5 percent by weight of said composition.

The present invention also relates to the compounds of formula I which can be considered as derivatives of benzylidene camphor of the formula

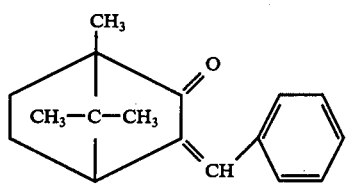

which itself is a good filtering agent for light rays and which is described in French Pat. No. 2,004,142.

The compound of formula (I) exhibit very interesting solubility properties and in certain media or vehicles the compounds of formula (I) have a significantly better solubility than does benzylidene camphor.

It is known, for instance, that the use of known filtering agents with conventional cosmetic vehicles is often limited by the insufficient solubility characteristics of these filtering agents. However, a significant number of the compounds of formula I are particularly efficacious because their solubility in water or in a hydroalcoholic medium is markedly superior to some of the more conventionally employed filtering agents. To illustrate this point, the following table gives solubility values in water, ethanol and a 50:50 water-ethanol mixture for the following compounds:

A. 4-[(2-oxo-3-bornylidene)methyl]-phenyl trimethylammonium methyl sulfate (compound of formula I), B. 4-[(2-oxo-3-bornylidene)methyl]-phenyl trimethylammonium paratoluene sulfonate (compound of Formula I), C. 4-[(2-oxo-3-bornylidene)methyl]-phenyl trimethylammonium methane sulfonate (compound of Formula I), D. 4-[(2-oxo-3-bornylidene)methyl]-phenyl trimethylammonium chloride (compound of Formula I), and E. 1,7,7-trimethyl-3-benzylidene [2,2,1] bicyclo-2-heptanone (benzylidene camphor - compound of Formula II conventional anti-solar agent).

|  | A | B | C | D | E |
|---|---|---|---|---|---|
| Solubility in 100 cc of $H_2O$ | 100% | 0.2% | 50% | 80% | insoluble |
| Solubility in 100 cc of ethanol | 70% | 1% | 50% | 95% | 14% |
| Solubility in 50 cc $H_2O$ |  |  |  | (I) |  |
| 50 cc ethanol | 100% | 10% | 50% | 120% | 0.5% |

It can thus be seen that the compounds of the present invention have generally better solubility characteristics in water and in a 50—50 water-ethanol solution than does benzylidene camphor. Further these solubility characteristics of the compounds of the invention are not accompanied by a weak retention level thereof on the skin. To the contrary, the compounds of this invention exhibit a remarkable improvement in their substantivity for the skin.

That the compounds of formula (I) of the present invention exhibit highly desirable light ray absorption characteristics can be seen in the table below which gives percent transmission data for two representatives compounds of formula (I) (A and B, as defined above) each in a 1.5% solution in ethanol (96° titer) at a thickness of 0.01 mm.

| $\lambda$ Millimicrons | A % transmitted | B % transmitted |
|---|---|---|
| 270 | 12 | 30 |
| 275 | 9 | 21 |
| 280 | 8 | 20 |
| 285 | 7.5 | 19 |
| 290 | 8 | 20 |
| 295 | 14 | 30 |
| 300 | 19 | 41 |
| 310 | 40 | 58 |
| 320 | 86 | 85 |

Further it has been found that the compounds of formula (I) possess good thermal and photochemical stability properties. For instance, a three hour exposure to an ultra violet sun lamp, or exposure to light for a period of a week at 60° C did not modify the transmission curve. Moreover, the results of dermotoxicity tests confirmed the harmlessness of these compounds.

The compounds of formula (I) can be prepared according to the method of Haller by condensation in an inert solvent such as benzene, toluene, ether, dimethylformamide and dimethoxyethane, of a p-dimethyl amino benzoic aldehyde, substituted or not, on the sodium salt of camphor, prepared by the reaction of camphor with sodium or a strong base such as sodium alcoholate, sodium amide or sodium hydride. The resulting product is then subjected to a quaternization or to a salification operation.

EXAMPLE 1

Preparation of 1,7,7-trimethyl-4-dimethylamino-3-benzylidene (2,2,1) bicyclo-2-heptanone, i.e. 4-dimethylamino benzylidene camphor having the formula

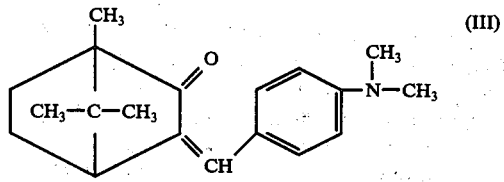

There is heated to reflux for 30 minutes in anhydrous toluene, 577.5 g (3.8 moles) of snythesized camphor and 205 g of sodium methylate. After cooling to ambient temperature, 566 g of p-dimethylaminobenzaldehyde are added all at once. The resulting mixture is then heated for 4 hours at reflux, after which it is cooled to ambient temperature. The reaction mixture is then extracted with water and the toluene fraction is recovered and evaporated to dryness, yielding 1013 g of a solid yellow residue. This residue is then recrystallized in absolute ethanol, yielding 711 g of bright yellow crystals melting at 110° C.

| Elemental Analysis: | C% | H% | N% |
|---|---|---|---|
| Calculated | 80.56 | 8.83 | 4.94 |
| Found | 80.54 | 9.04 | 4.87 |

The compounds of formula (I) are obtained starting with the 4-dimethylamino benzylidene camphor of formula (III) produced in Example 1 by subsequent quaternization or salification.

Representative quaternizing agents that can be employed include:
a. alkyl sulfates, such as methyl sulfate or ethyl sulfate;
b. alkyl substituted alkylsulfonates, such as methyl methane sulfonate, and
c. alkyl substituted arylsulfonates, such as methyl-p-toluenesulfonate or methyl bromobenzene sulfonate.

The anion X⁻ in structural formula (I) can also be obtained by anion exchange, for example, by passing a compound of formula (I) over an anion exchange resin containing an anion other than X⁻.

The composition of the present invention can also contain one or more water-soluble protective agents of formula (I) in combination with other filtering agents, as for example, one or more other water-soluble filtering or anti-solar agents or even one or more fat-soluble antisolar agents.

When the compositions of the present invention are provided in the form of an emulsion, the presence of both water-soluble and fat-soluble anti-solar agents is very advantageous since protection is obtained simultaneously for both the aqueous phase and for the oil phase of the emulsion.

Further, it has been observed that the highly desirable affinity characteristics of the composition of this invention for the skin can be improved even further when the composition also contains other water-soluble anti-solar agents which are less substantive to the skin than those of the present invention.

The examples hereafter illustrate the preparation and application of the compounds of formula (I).

Examples of Preparation

EXAMPLE 2

Preparation of 4-[(2-oxo-3-bornylidene)methyl]-phenyl trimethylammonium methyl sulfate of the formula:

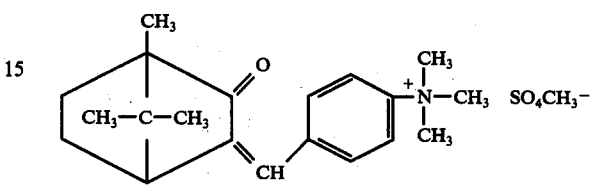

750 g of 4-dimethylamino benzylidene camphor (prepared in Example 1) and 334 g of methyl sulfate are progressively heated to reflux in ethyl acetate. An exothermic precipitation suddenly occurs and when it has abated the reaction mixture is then heated for three hours at reflux. A pale yellow solid precipitates which is then filtered, washed with ethyl acetate and recrystallized in a benzene-acetonitrile mixture, yielding 866 g of white product melting at 20° C.

| Elemental analysis: | C₂₁H₃₁NO₅S | | MW = 409 | |
|---|---|---|---|---|
| | C% | H% | N% | S% |
| Calculated: | 61.61 | 7.58 | 3.42 | 7.82 |
| Found: | 61.31 | 7.75 | 3.40 | 7.93 |

EXAMPLE 3

Preparation of 4-[(2-oxo-3-bornylidene)methyl]phenyl trimethylammonium paratoluene sulfonate of the formula:

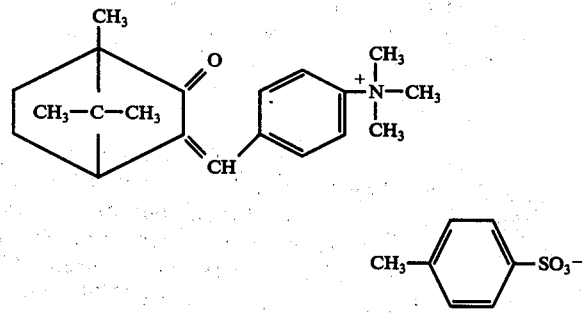

There are heated for 8 hours at reflux, in toluene and with good agitation, 283 of 4-dimethylamino benzylidene camphor (prepared in Example 1) and 186 g of methyl paratoluenesulfonate. A white solid which precipitates is then filtered and dried, yielding 417 g of product which after recrystallization in ethanol gives 362 g of white crystals, having a melting point of 305° C.

| Elemental analysis: C₂₇H₃₅NO₄S | | | |
|---|---|---|---|
| | C% | H% | N% |
| Calculated: | 69.08 | 7.46 | 2.98 |

-continued

Elemental analysis: $C_{27}H_{35}NO_4S$

| | C% | H% | N% |
|---|---|---|---|
| Found: | 69.08 | 7.50 | 2.90 |

EXAMPLE 4

Preparation of 4-[(2-oxo-3-bornylidene)methyl]-phenyl trimethylammonium methane sulfonate of the formula

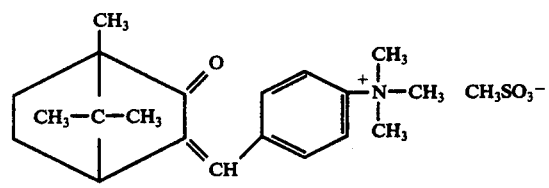

There is heated for ten hours at reflux and with good agitation a mixture of 28.3 g of 4-dimethylamino benzylidene camphor prepared in Example 1 and 16.5 g of methyl methane sulfonate in 50 ml of toluene. The precipitate which forms is then filtered and washed with toluene and then crystallized in a mixture of benzene and acetonitrile, yielding 26.6 g of white crystals melting at 265° C.

Analysis: $C_{21}H_{31}NO_4S$

| | C% | H% | N% |
|---|---|---|---|
| Calculated: | 64.12 | 7.88 | 3.56 |
| Found: | 64.16 | 7.62 | 3.53 |

EXAMPLE 5

Preparation of 4-[(2-oxo-3-bornylidene)methyl]-phenyl trimethylammonium chloride of the formula:

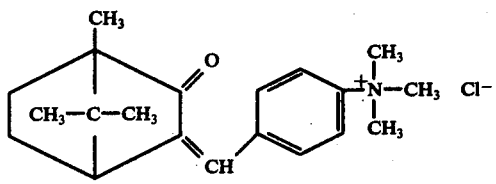

A solution of 10 g of anti-solar agent prepared in Example 2 in 20 ml of water is deposited on an anion exchange resin in the form of the chloride ion. The resin is then eluted with water and the resulting eluates are concentrated by drying under reduced pressure. The solid residue thus obtained is crystallized in a mixture of ethanol and benzene yielding 6.4 g of white crystals melting at 240° C are recovered.

Analysis: $C_{20}H_{28}ClNO$

| | C% | H% | N% | Cl% |
|---|---|---|---|---|
| Calculated: | 71.96 | 8.39 | 4.19 | 10.64 |
| Found: | 71.78 | 8.37 | 4.11 | 10.84 |

EXAMPLE 6

Preparation of 3-methyl-4-[(2-oxo-3-bornylidene)methyl[-phenyl trimethylammonium methyl sulfate.

Step (a): preparation of 1,7,7-trimethyl-3(4-dimethylamino-2-methyl benzylidene)[2,2,1] bicyclo-2-heptanone of the formula:

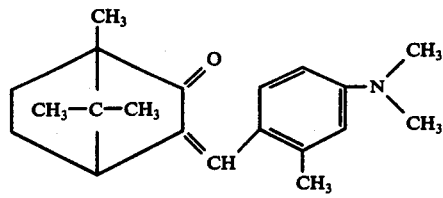

2.3 g of sodium are vigorously agitated in 100 ml of boiling toluene. The toluene is then decanted and the resulting sodium beads are recovered with 100 ml of anhydrous sulfuric ether. There are then added to the thus recovered sodium beads, with agitation and while maintaining the temperature at 25° C by cooling, 15.2 g of camphor. When all the sodium has reacted (4 to 5 hours), the reaction mixture is cooled to 0° C. 16.3 g of 4-dimethylamino-2-methyl benzoic aldehyde are then added and the resulting mixture is agitated initially for 3 hours at 0° C and then for 30 minutes at the reflux of the ether. The reaction mixture is then cooled at which point 100 ml of water are added thereto. The ether phase is then separated and dried on sodium sulfate, after which the ether is evaporated. The resulting oily residue is fractionated and the fraction (23.8 g) distilling at 243° C under 1 mm Hg is recovered and can be purified by crystallization in sulfuric ether to provide yellow crystals melting at 115° C.

Elemental analysis: $C_{20}H_{27}NO$

| | C% | H% | N% |
|---|---|---|---|
| Calculated: | 80.81 | 9.09 | 4.71 |
| Found: | 80.88 | 8.83 | 4.59 |

Step (b): preparation of 3-methyl-4-[(2-oxo-3-bornylidene)methyl]-phenyl trimethylammonium methyl sulfate of the formula

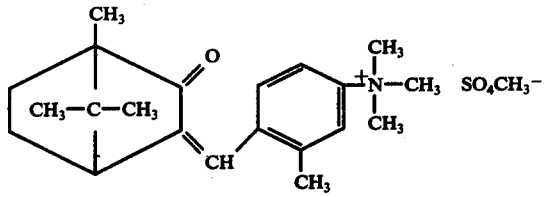

14.9 g of the compound prepared in step (a) and 6.3 g of methyl sulfate are progressively heated in ethyl acetate to reflux for 3 hours. The resulting white solid is then filtered and washed with ethyl acetate, yielding 12 g of white crystals melting at 245° C.

Elemental analysis: $C_{22}H_{33}NO_5S$

| | C% | H% | N% | S% |
|---|---|---|---|---|
| Calculated: | 62.41 | 7.80 | 3.31 | 7.56 |
| Found: | 61.78 | 7.88 | 3.24 | 7.63 |

EXAMPLE 7

Preparation of 3-chloro-4-[(2-oxo-3-bornylidene)methyl] phenyl trimethylammonium methyl sulfate.

Step (a): preparation of 1,7,7-trimethyl-3-(4-dimethylamino-2-chloro benzylidene)-[2,2,1]-bicyclo-2-heptanone of the formula

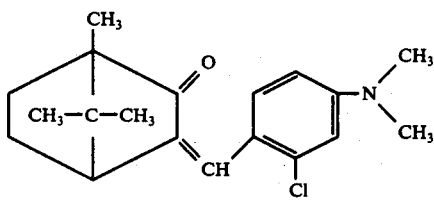

A mixture of 76 g of camphor and 19.5 g of sodium amide in 150 ml of dry toluene is agitated for 3 hours at reflux. After cooling to ambient temperature, there are then added 92 g of O-chloro-p-dimethylamino benzaldehyde. The resulting mixture is then heated at reflux for 5 hours. Thereafter the mixture is cooled and to the cooled mixture there is added about 400 ml of water. Then the toluene phase is separated, dried and concentrated to dryness. The resulting residue is crystallized in isopropanol, yielding 82 g of yellow crystals melting at 128° C.

| Elemental analysis: $C_{19}H_{24}NOCl$ | | | |
|---|---|---|---|
| | C% | H% | N% |
| Calculated: | 71.81 | 7.56 | 4.41 |
| Found: | 71.53 | 7.90 | 4.38 |

Step (b): preparation of 3-chloro-4-[(2-oxo-3-bornylidene)methyl]-phenyl trimethylammonium methyl sulfate of the formula:

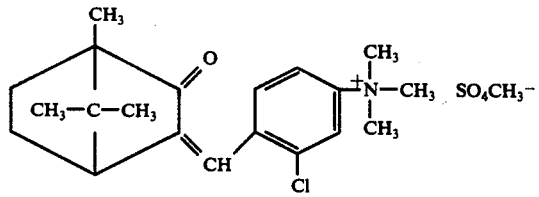

There is heated at reflux for 12 hours a mixture of 42 g of the product of step (a) and 15.2 g of methyl sulfate in 400 ml or acetonitrile. The resulting precipitate is then filtered and crystallized in a mixture of benzene and acetonitrile, yielding pale yellow platelets melting at 210° C.

| Elemental analysis: $C_{21}H_{30}NO_5Cl\ S$ | | |
|---|---|---|
| | N% | S% |
| Calculated: | 3.16 | 7.19 |
| Found: | 3.12 | 7.18 |

EXAMPLE 8

Preparation of 4-[2-oxo-3-bornylidene) methyl]-phenyl trimethyl ammonium camphorsulfonate of the formula:

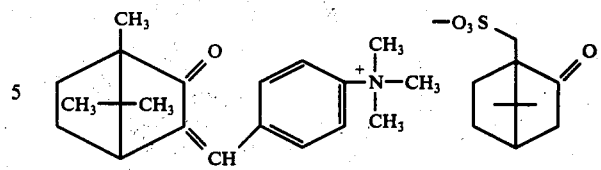

There are heated for 15 hours at reflux, in 300 ml of ethyl acetate and with good agitation, 56.6 g of 4-dimethylaminobenzylidene-camphor (prepared in example 1) and 49.2 g of methyl camphor sulfonate. After cooling to ambiant temperature the precipitate is then filtered and washed with ethyl acetate and then recrystallized in a mixture of toluene-acetonitrile, yielding 73 g of snow white crystals melting at 265° C.

| Analysis: $C_{30}H_{43}O_5NS$ | | | | |
|---|---|---|---|---|
| | C% | H% | N% | S% |
| Calculated: | 68.05 | 8.13 | 2.64 | 6.05 |
| Found: | 68.00 | 8.11 | 2.51 | 6.29 |

EXAMPLE 9

Preparation of 4-[(2-oxo-3-bornylidene) methyl]-phenyl dimethyl ethyl ammonium ethyl sulfate of the formula:

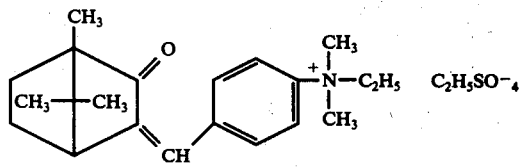

There are heated for 6 hours at reflux, in 100 ml of ethyl acetate and with good agitation, 14 g of 4-dimethylamino-benzylidene-camphor (prepared in example 1) and 8 g of diethyl sulfate.

After cooling to ambiant temperature the precipitate is then filtered and washed with ethyl acetate, yielding 9.9 g of hydroscopic white crystals melting at 126°–127° C.

| Analysis: | N% | S% |
|---|---|---|
| Calculated: | 3.21 | 7.32 |
| Found: | 2.93 | 7.52 |

EXAMPLE 10

Preparation of 4-[(2-oxo-3-bornylidene)methyl]-phenyl dimethyl dodecylammonium paratoluene sulfonate of the formula:

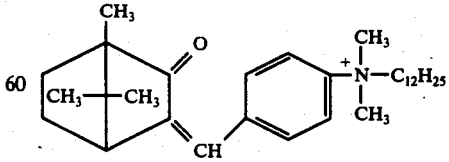

There are heated for 6½ hours at a temperature of 130°–140° C, 2.8 g of 4-dimethylamino-benzylidene-camphor (prepared in example 1) and 3.4 g of lauryl tosylate.

The whole reaction mixture is then dissolved in a sufficient quantity of isopropanol; then the isopropanol is evaporated, yielding 4.6 g of whity crystals of the product of the above formula melting at 135° C.

| Analysis: | N% | S% |
|---|---|---|
| Calculated: | 2.25 | 5.13 |
| Found: | 2.32 | 5.69 |

The compounds in which R represents an atom of H are obtained by protonisation of the tertiary amine corresponding to the compounds of the formula (I), for instance by reaction with a strong acid.

Examples of Use

EXAMPLE 11

An anti-solar lotion is prepared as follows:

| | |
|---|---|
| Lanolin | 2.5 g |
| Butylhydroxy anisole | 0.025 g |
| Butyl hydroxytoluene | 0.025 g |
| Octyl gallate | 0.0125 g |
| Triglyceride of fatty acid having 8–12 carbon atoms | 40 g |
| Perfume | 1.25 g |
| 4-[(2-oxo-3-bornylidene)methyl]-phenyl trimethylammonium methylsulfate | 4 g |
| Ethanol (96° titer), q.s.p. | 100 g |

EXAMPLE 12

| | |
|---|---|
| Glycerine | 5 g |
| Polyethylene glycol (MW = 400) | 0.5 g |
| Ethoxylated lanolin | 1 g |
| Perfume (soluble) | 2 g |
| 4-[(2-oxo-3-bornylidene)methyl]-phenyl trimethylammonium methylsulfate | 2 g |
| Ethyl alcohol (96° titer) | 50 g |
| Water, q.s.p. | 100 g |

EXAMPLE 13

An anti-solar aerosol formulation is prepared as follows:

| | |
|---|---|
| Absolute ethyl alcohol | 30 g |
| Isopropyl myristate | 20 g |
| Ricin oil | 2 g |
| Lanolin | 5 g |
| Perfume | 1 g |
| 4-[(2-oxo-3-bornylidene)methyl]-phenyl trimethylammonium methylsulfate | 2 g |
| Dichlorodifluoromethane | 40 g |

The above composition was packaged in a conventional aerosol container under pressure.

EXAMPLE 14

An anti-solar aerosol foam composition is prepared as follows:

| | |
|---|---|
| Sipol wax | 3.5 g |
| Vaseline oil | 6 g |
| Isopropyl myristate | 3 g |
| Preservative ("Nipa ester 82521) (mixture of methyl, ethyl, butyl and benzyl ester of hydroxyl benzoic acid) | 0.3 g |
| Glycerine | 10 g |
| Perfume | 0.3 g |
| 4-[(2-oxo-3-bornylidene)methyl]-phenyl trimethylammonium methylsulfate | 2.5 g |
| Water, q.s.p. | 100 g |
| Dichlorodifluoromethane | 15 g |

The above composition was packaged in a conventional aerosol container under pressure.

EXAMPLE 15

An anti-solar lotion is prepared as follows:

| | |
|---|---|
| Cetyl stearyl alcohol | 2 g |
| Glycerol monostearate | 4 g |
| Cetyl alcohol | 4 g |
| Vaseline oil | 5 g |
| Butyl stearate | 5 g |
| Propylene glycol | 7 g |
| Silicone oil | 0.125 g |
| Ethylene oxide polymer having a molecular weight of 100,000–1,000,000, sold under the tradename "POLYOX" | 3.5 g |
| Preservative ("Nipa ester 82521) | 0.3 g |
| Perfume | 0.4 g |
| 4-[(2-oxo-3-bornylidene)methyl]-phenyl trimethylammonium methylsulfate | 4 g |
| Water, q.s.p. | 100 g |

EXAMPLE 16

An anti-solar milk is prepared as follows:

| | |
|---|---|
| Sipol wax | 5 g |
| Vaseline oil | 6 g |
| Isopropyl myristate | 3 g |
| Silicone oil | 1 g |
| Cetyl alcohol | 1 g |
| Glycerine | 20 g |
| Preservative ("Nipa ester 82521) | 0.3 g |
| Perfume | 0.3 g |
| 4-[(2-oxo-3-bornylidene)methyl]-phenyl trimethylammonium methylsulfate | 3 g |
| Water, q.s.p. | 100 g |

EXAMPLE 17

A colored hair setting lotion is prepared as follows:

| | |
|---|---|
| Copolymer of vinylpyrrolidone-Vinyl acetate (70/30) MW 40.000 | 2 g |
| Dye-Blue Victoria BSA CI 44045 | 0.001 g |
| Ethyl alcohol | 50 g |
| Triethanolamine, q.s.p. | pH 7 |
| 4-[(2-oxo-3-bornylidene)methyl]-phenyl trimethylammonium methylsulfate | 0.2 g |
| Water, q.s.p. | 100 cc |

EXAMPLE 18

A colored hair setting lotion is prepared as follows:

| | |
|---|---|
| Copolymer of crotonic acid - vinyl acetate (10/90) MW 50.000 with a viscosity of 7–9 cps at 35° C in a 5% | 2 g |

-continued

| | |
|---|---|
| in weight solution of tetrachloroethan. | |
| Dye - CI Basic Violet No. 3 | |
| CI 42555 | 0.01 g |
| Ethyl alcohol | 50 g |
| Triethanolamine, q.s.p. | pH 7 |
| 4-[(2-oxo-3-bornylidene)methyl]- phenyl trimethylammonium paratoluene sulfonate | 0.2 g |
| Water, q.s.p. | 100 cc |

EXAMPLE 19

An anti-solar milk having a medium protective action is prepared as follows:

| | |
|---|---|
| Cetyl stearyl alcohol condensed with 25 moles of ethylen oxide | 5 g |
| Cetyl alcohol | 1 g |
| 2-octyl dodecyl alcohol | 15 g |
| "Codex" type vaseline oil | 5 g |
| Insaponifiables of Lucern | 0.2 g |
| Benzylidene-camphor | 1 g |
| 4-[(2-oxo-3-bornylidene)methyl]-phenyl trimethylammonium methylsulfate | 2.5 g |
| Preservative "Nipa ester 82 521" (mixture of methyl, ethyl, butyl and benzyl - ester of p-hydroxy benzoic acid) | |
| Perfume | 0.5 g |
| Water q.s.p. | 100 g |

EXAMPLE 20

An anti-solar cream having a strong protective action is prepared as follows:

| | |
|---|---|
| Hydrogenated polyoxyethylenated palm oil | 5 g |
| Cetyl stearyl alcohol condensed with 15 moles of ethylen oxide | 5 g |
| Lanolin | 3 g |
| Alcohols of lanolin | 1 g |
| Turnesol oil | 5 g |
| Vaseline oil | 10 g |
| Benzylidene camphor | 2.5 g |
| 4-[(2-oxo-3-bornylidene)methyl]-phenyl trimethyl-ammonium methylsulfate | 4 g |
| Preservative "Nipa ester 82521" q.s. | |
| Propylen glycol | 5 g |
| Perfume | 0.5 g |
| Water q.s.p. | 100 g |

Every compound or mixture of compounds of formula (I) may be utilised in every one of the cosmetic compositions of the examples 11 to 20 in amounts of 0.05-10 percent by weight of said compositions.

What is claimed is:

1. A cosmetic composition comprising a solution of
   1. a solvent which is water, lower alkanol, lower polyol or an aqueous solution of a lower alkanol
   2. an antisolar agent of the formula

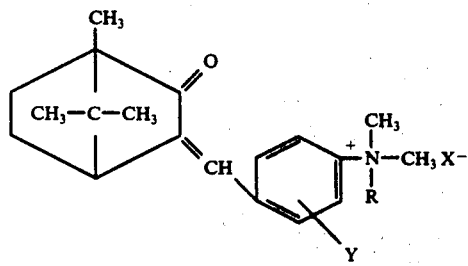

wherein

R is selected from the group consisting of hydrogen and alkyl containing 1-12 carbon atoms;

Y is selected from the group consisting of halogen, methyl and hydrogen; and

X is selected from the group consisting of chloride, p-toluene sulfonate, methyl bromobenzene sulfonate, methane sulfonate, camphosulfonate, methylsulfate and ethylsulfate; wherein said anti-solar agent is present in amounts of about 0.05-10 percent by weight of said composition.

2. The composition of claim 1 wherein said anti-solar agent is present in amounts of about 0.05-5 percent by weight of said composition.

3. The composition of claim 2 which also includes 0.001-0.01 percent of a photosensitive dye which is a derivative of triphenylmethane.

4. The composition of claim 1 wherein said anti-solar agent is in solution in a solvent selected from the group consisting of water, lower alkanol and an aqueous solution of a lower alkanol, wherein said lower alkanol is ethanol or isopropanol.

5. The composition of claim 4 wherein said lower alkanol is ethanol.

6. The composition of claim 1 which also includes an aerosol propellant and said composition is packaged under pressure in an aerosol container.

7. The composition of claim 1 which also includes benzylidene camphor in amounts from 1% to 2.5% of said composition.

8. A process for protecting cosmetic composition susceptible of being altered by light rays, comprising incorporating into said compositions a compound of the formula:

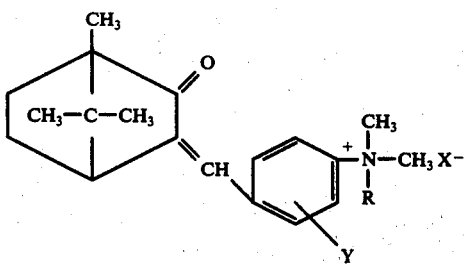

wherein

R is selected from the group consisting of hydrogen and alkyl containing 1-12 carbon atoms;

Y is selected from the group consisting of halogen methyl and hydrogen; and

X is selected from the group consisting of chloride, p-toluene sulfonate, methyl bromobenzene sulfonate, methane sulfonate, camphosulfonate, methylsulfate and ethylsulfate; wherein said anti-solar agent is present in amounts of about 0.05-10 percent by weight of said composition, said compound being incorporated in amounts of 0.05-5 percent by weight of said composition.

9. A compound of the formula:

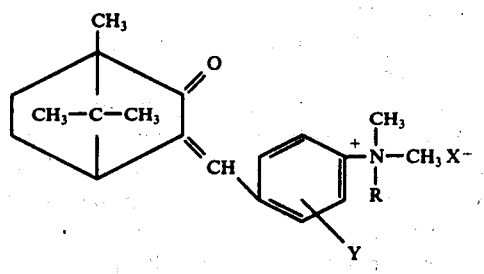

wherein

R is selected from the group consisting of hydrogen and alkyl containing 1–12 carbon atoms;

Y is selected from the group consisting of halogen, methyl and hydrogen; and

X is selected from the group consisting of halide, arylsulfonate, alkylsulfonate, camphosulfonate and alkylsulfate.

10. The composition of claim 1, wherein said said lower polyol selected from the group consisting of propylene glycol, glycerol, and sorbitol.

11. The composition of claim 1, wherein said antisolar agent is 4-[(2-oxo-3-bornylidene) methyl]-phenol trimethylammonium methyl sulfate.

12. The composition of claim 1, wherein said solvent is water.

13. The composition of claim 1, wherein said solvent is lower alkanol.

* * * * *